United States Patent [19]
Carling et al.

[11] Patent Number: 5,972,919
[45] Date of Patent: *Oct. 26, 1999

[54] COMBINATION OF A BRONCHODILATOR AND A STEROIDAL ANTI-INFLAMMATORY DRUG FOR THE TREATMENT OF RESPIRATORY DISORDERS, AS WELL AS ITS USE AND THE PREPARATION THEREOF

[75] Inventors: Christer Carl Gustav Carling, Dalby; Jan William Trofast, Lund, both of Sweden

[73] Assignee: Astra Aktiebolag, Sodertalje, Sweden

[ * ] Notice: This patent is subject to a terminal disclaimer.

[21] Appl. No.: 08/944,683

[22] Filed: Oct. 7, 1997

Related U.S. Application Data

[63] Continuation of application No. 08/317,407, Oct. 3, 1994, Pat. No. 5,674,860, which is a continuation of application No. 07/992,089, Dec. 17, 1992, abandoned.

[30] Foreign Application Priority Data

Dec. 18, 1991 [EP] European Pat. Off. .............. 91311761

[51] Int. Cl.$^6$ .......................... A61K 31/56; A61K 31/135
[52] U.S. Cl. .......................... 514/171; 514/174; 514/653; 514/826
[58] Field of Search ................................... 514/171, 174, 514/653, 826

[56] References Cited

U.S. PATENT DOCUMENTS 3,983,233 9/1976 Brattsand et al. .
3,994,974 11/1976 Murakami et al. .

FOREIGN PATENT DOCUMENTS 0 416 950 3/1991 European Pat. Off. .
0 416 951 3/1991 European Pat. Off. .

OTHER PUBLICATIONS

Salonen, Acta Pharmacologica et Toxicologica 57, 1–33 (1985).
Svedmyr, Am. Rev. Resp. Dis. 141, S31–S38 (1990).
Horn, et al., Resp. Med. 84, 61–66, 67–70 (1990).
Källström, et al., Agents and Actions 17, 355–357 (1985).
Kubin, et al., Int. Arch. Allergy Immunol. 98, 266–272 (1992).
Brattsand, et al., Int. J. Microcirc. Clin. Exp. 5, 263 (1986).
Claman, New England J. Med. 287, 388–397 (1972).
Marsac, et al., Annals of Allergy 63, 220–224 (1989).
Maesen, et al., Chest 97, 590–594 (1990).
McDonald, et al., Current Medical Research and Opinion 11, 116–122 (1988).
Bond, New Zealand Medical Journal, p. 369, Aug. 28, 1991.
Dahl, et al., J. Allergy Clin. Immunol. 83, 811–815 (1989).
Dal Negro, et al., Current Therapeutic Research 35, 561–565 (1984).
Wallin, et al., Thorax 45, 259–261 (1990).
Lorentzson, et al., Thorax 45, 733–735 (1990).
Ebden, et al., Thorax 41, 869–874 (1986).
Morris, et al., J. Allergy Clin. Immunol. 75, 1–14 (1985).
Holst, et al., New Zealand Medical Journal 79, 769–773 (1974).
Morris, et al., Chest 88, 133S–141S (1985).
Flenley, Respiration 55, 4–9 (1989).
Lurie, et al., Lung Suppl., 154–167 (1990).
Paterson, et al., Am. Rev. Resp. Dis. 120, 1149–1188 (1979).
O'Loughlin, Postgraduate Medicine 82, 231–238 (1987).
Stafford, Postgraduate Medicine 84, 85–98 (1988).
Lacronique, et al., Rev. Mal. Resp. 6, 15–30 (1989).
Quaglia, et al., Folia Allergol. Immunol. Clin. 24, 318–327 (1977).
Lorentzen et al., Thorax 45, 733–735, 1990.
Marsac, "Inhaled beta agonists and inhaled steroids in the treatment of asthma", Ann. of Allergy, 63(3), pp. 220–224, 1989.
Svedmyr, "The Current Place of beta–Agonists in the management of Asthma", Lung (USA), 168, pp. 105–110, 1990.

*Primary Examiner*—Raymond Henley, III
*Attorney, Agent, or Firm*—White & Case L.L.P.

[57] ABSTRACT

Effective amounts of formoterol (and/or a physiologically acceptable salt and/or solvate thereof) and budesonide are used in combination for simultaneous, sequential or separate administration by inhalation in the treatment of respiratory disorder.

19 Claims, No Drawings

COMBINATION OF A BRONCHODILATOR AND A STEROIDAL ANTI-INFLAMMATORY DRUG FOR THE TREATMENT OF RESPIRATORY DISORDERS, AS WELL AS ITS USE AND THE PREPARATION THEREOF

This application is a continuation of application Ser. No. 08/317,407, filed on Oct. 3, 1994, now U.S. Pat. No. 5,674,860, which is a continuation of application Ser. No. 07/992,089, filed Dec. 17, 1992 now abandoned.

FIELD OF THE INVENTION

This invention relates to improvements in the treatment of mild as well as severe asthma and other respiratory disorders. More particularly, it relates to the use of a bronchodilator in combination with a steroidal anti-inflammatory drug for the treatment of respiratory disorders such as asthma, and to pharmaceutical compositions containing the two active ingredients. It emphasizes the use of a long-acting bronchodilator which provides rapid relief of symptoms.

BACKGROUND OF THE INVENTION

There have recently been significant advances in our understanding of asthma. Despite many advances, both in awareness of the disease by doctors and patients alike, coupled with the introduction of very powerful and effective anti-asthma drugs, asthma remains a poorly understood and often poorly treated disease. Previously, contraction of airway smooth muscles has been regarded as the most important feature of asthma. Recently there has been a marked change in the way asthma is managed, stemming from the fact that asthma is recognized as a chronic inflammatory disease. Uncontrolled airway inflammation may lead to mucosal damage and structural changes giving irreversible narrowing of the airways and fibrosis of the lung tissue. Therapy should therefore be aimed at controlling symptoms so that normal life is possible and at the same time provide basis for treating the underlying inflammation.

The most common cause for poor control of asthma is poor compliance with the long-term management of chronic asthma, particularly with prophylactic treatments, such as inhaled steroids, which do not give immediate symptom relief. Patients will readily take $\beta_2$-agonist inhalers, since these provide rapid relief of symptoms, but often do not take prophylactic therapy, such as inhaled steroids, regularly because there is no immediate symptomatic benefit. They also counteract down regulation of $\beta_2$-adrenoceptor agonists.

Formoterol, (N-[2-hydroxy-5-[1-hydroxy-2-[[2-(4-methoxyphenyl)-1-methylethyl]amino]ethyl]phenyl] formamide), is an adrenoceptor agonist which selectively stimulates $\beta_2$-receptors, thus producing relaxation of bronchial smooth muscle, inhibition of the release of endogenous spasmogens, inhibition of oedema caused by endogenous mediators, and increased mucociliary clearance. Inhaled formoterol fumarate acts rapidly, usually within minutes which gives the patient immediate confirmation that he has taken an adequate dose and thereby avoiding overdosing of both $\beta$-agonist and steroid. Inhaled formoterol also exerts a prolonged bronchodilation, which in clinical trials has been demonstrated as up to 12 hours.

Budesonide, (16,17-butylidenebis(oxy)-11,21-dihydroxypregna-1,4-diene-3,20-dione), may be given in a high inhaled dose (up to 2 mg daily) with very low systemic effects, possibly because of its rapid metabolism. The high rapid systemic elimination of budesonide is due to extensive and rapid hepatic metabolism. Long term clinical studies have shown that inhaled budesonide is a pharmacologically safe drug. High doses of inhaled budesonide are highly effective and well tolerated when used in oral steroid replacement therapy. Budesonide represents a logical safe and effective therapy for long term control of asthma.

The inhaled route of administration enables the dose to be delivered directly to the airways. By this type of administration, it is possible to give a small dose and thereby minimizing unwanted side-effects. The drawbacks of the currently available bronchodilators are their relatively short duration of action. By using a compound with long duration e.g. formoterol it would be possible to avoid the nocturnal asthma, which so often causes considerable anxiety and debility to the patients. Formoterol gives less nocturnal waking than the commonly used short-acting agonists like salbutamol, terbutaline and the like. Formoterol has been registered for oral administration in Japan since 1986.

Pharmaceutical combinations of long-acting $\beta_2$-agonists and steroids are disclosed in two European applications, EP 416950 which discloses the combination of salmeterol and beclomethasone, and EP 416951 which discloses the combination of salmeterol and fluticasone propionate.

In Ann. Allergy 1989, 63 (3), p. 220–224 the use of a $\beta$2-agonist, i.e. formoterol and a steroid, i.e. budesonide separately are mentioned. Not disclosed is a pharmaceutical combination including both formoterol and budesonide, or the use of the two compounds in combination therapy. The use of a $\beta_2$-agonist and a steroid separately is also mentioned in Lung (1990), 168, no. supp, p. 105–110.

OUTLINE OF THE INVENTION

The present invention is based on the concept of a novel combination therapy whereby formoterol (and/or a physiologically acceptable salt and/or solvate thereof) and budesonide are administered simultaneously, sequentially or separately by inhalation. This combination has not only a greater efficiency and duration of bronchodilator action but the combination also has a rapid onset of action. This new feature is of utmost importance in order to establish a higher compliance for patients and it provides a rescue medicine thereby avoiding the necessity for the patient of carrying two different inhalers. This simplifies life for patients considerably and makes life more comfortable and secure. The rapid onset of the long-acting $\beta_2$-agonist gives the patient immediate confirmation that he has taken an adequate dose and thereby avoiding overdosing of both $\beta_2$-agonist and steroid. Since the use of formoterol instead of salmoterol gives a much more rapid onset the combinations according to the invention have a number of advantages compared to the combinations disclosed i EP 416950 and EP 41651. The combination according to present invention permits a twice daily dosing regime as a basic treatment of asthma, particularly nocturnal asthma.

The present invention provides a medicament containing, separately, or together, (i) formoterol (and/or a physiologically acceptable salt and/or solvate thereof) and (ii) budesonide for simultaneous, sequential or separate administration by inhalation in the treatment of respiratory disorders.

The invention also provides a pharmaceutical composition for administration by inhalation in the treatment of respiratory disorders which composition comprises formoterol (and/or a physiologically acceptable salt and/or solvate thereof) and budesonide.

According to another aspect of the invention there are provided pharmaceutical compositions comprising effective amounts of formoterol (and/or a physiologically acceptable salt and/or solvate thereof) and budesonide as a combined preparation for simultaneous, sequential or separate administration by inhalation in the treatment of respiratory disorder.

The invention further provides formoterol (and/or a physiologically acceptable salt and/or solvate thereof) and budesonide for use in combination therapy by simultaneous, sequential or separate administration by inhalation in the treatment of respiratory disorders.

Further the invention provides the use of formoterol (and/or a physiologically acceptable salt and/or solvate thereof) in the manufacture of a medicament for combination therapy where formoterol (and/or a physiologically acceptable salt and/or solvate thereof) and budesonide are administered simultaneously, sequentially or seperately by inhalation in the treatment of respiratory disorder and the use of budesonide in the manufacture of a medicament for combination therapy where formoterol (and/or a physiologically acceptable salt and/or solvate thereof) and budesonide are administered simultaneously, sequentially or separately by inhalation in the treatment of respiratory disorders.

The invention additionally relates to the use of formoterol (and/or a physiologically acceptable salt and/or solvate thereof) and budesonide in the manufacture of a medicament for combination therapy for simultaneous, sequential or separate administration of formoterol and budesonide by inhalation in the treatment of respiratory disorders.

According to a further feature of the invention there is provided a method of treating respiratory disorder which comprises the simultaneous, sequential or separate administration by inhalation of effective amounts of formoterol (and/or a physiologically acceptable salt and/or solvate thereof) and budesonide.

Suitable physiologically salts of formoterol include acid addition salts derived from inorganic and organic acids, such as the hydrochloride, hydrobromide, sulphate, phosphate, maleate, fumarate, tartrate, citrate, benzoate, 4-methoxybenzoate, 2- or 4-hydroxybenzoate, 4-chlorobenzoate, p-toluenesulphonate, methanesulphonate, ascorbate, salicylate, acetate succinate, lactate, glutarate, gluconate, tricarballylate, hydroxynaphthalenecarboxylate or oleate. Formoterol is preferably used in the form of its fumarate salt and as a dihydrate.

The ratio of formoterol to budesonide used according to the invention is preferably within the range of 1:4 to 1:70. The two drugs may be administered separately in the same ratio.

The intended dose regimen is a twice daily administration, where the suitable daily dose of formoterol is in the range of 6 to 100 $\mu$g with a preferred dose of 6–48 $\mu$g and the suitable daily dose for budesonide is 50 to 4800 $\mu$g with a preferred dose of 100–1600 $\mu$g. The particular dose used will strongly depend on the patient (age, weight etc) and the severity of the disease (mild, moderate, severe asthma etc).

For administration, the combination is suitably inhaled from a nebulizer, from a pressurized metered dose inhaler or as a dry powder from a dry powder inhaler (e.g. as sold under the trade mark Turbuhaler) or from a dry powder inhaler utilizing gelation, plastic or other capsules, cartridges or blister packs.

A diluent or carrier, generally non-toxic and chemically inert to the medicament e.g. lactose, dextran, mannitol or glucose or any additives that will give the medicament a desired taste, can be added to the powdered medicament.

Examples of the preparation of suitable dosage forms according to the invention include the following: Formoterol fumarate dihydrate and budesonide (optionally premicronized) are mixed in the proportions given above. The agglomerated, free-flowing micronized mixture may be filled into a dry powder inhaler such as sold under the trade mark Turbuhaler. When a capsule system is used, it is desirable to include a filler in the mixture.

The micronized mixture may be suspended or dissolved in a liquid propellant mixture which is kept in a container that is sealed with a metering valve and fitted into a plastic actuator. The propellants used may be chlorofluorocarbons of different chemical formulae. The most frequently used chlorofluorocarbon propellants are trichloromonofluoromethane (propellant 11), dichloro-difluoromethane (propellant 12), dichlorotetrafluoroethane (propellant 114), tetrafluoroethane (propellant 134a) and 1,1-difluoro-ethane (propellant 152a). Low concentrations of a surfactant such as sorbitan trioleate, lecithin, disodium dioctylsulphosuccinate or oleic acid may also be used to improve the physical stability.

The invention is further illustrated by way of example with reference to the following Examples.

EXAMPLE 1

Dry Powder Inhaler (Turbuhaler)

| Active ingredient | Per dose |
|---|---|
| Formoterol (as fumarate dihydrate) | 12 $\mu$g |
| Budesonide | 200 $\mu$g |

The storage unit of the inhaler is filled with sufficient material for at least 200 doses.

| Active ingredient | Per dose |
|---|---|
| Formoterol (as fumarate dihydrate) | 24 $\mu$g |
| Budesonide | 200 $\mu$g |

The storage unit is filled with sufficient material for at least 200 doses.

| Active ingredient | Per dose |
|---|---|
| Formoterol (as fumarate dihydrate) | 12 $\mu$g |
| Budesonide | 100 $\mu$g |

The storage unit is filled with sufficient material for at least 200 doses.

EXAMPLE 2

Metered Dose Inhaler

| Active ingredient | Per dose |
|---|---|
| Formoterol (as fumarate dihydrate) | 12 $\mu$g |
| Budesonide | 200 $\mu$g |
| Stabilizer | 0.1–0.7 mg |
| Propellant | 25–100 $\mu$l |
| Formoterol (as fumarate dihydrate) | 24 $\mu$g |
| Budesonide | 200 $\mu$g |
| Stabilizer | 0.1–0.7 $\mu$g |
| Propellant | 25–100 $\mu$l |

-continued

| Active ingredient | Per dose |
| --- | --- |
| Formoterol (as fumarate dihydrate) | 12 µg |
| Budesonide | 200 µg |
| Stabilizer | 0.1–0.7 mg |
| Propellant | 25–100 µl |

| Active ingredient | Per dose |
| --- | --- |
| Formoterol (as fumarate dihydrate) | 12 µg |
| Budesonide | 200 µg |
| Lactose | up to 5, 12.5 or 25 mg |
| Formoterol (as fumarate dihydrate) | 24 µg |
| Budesonide | 200 µg |
| Lactose | up to 5, 12.5 or 25 mg |
| Formoterol (as fumarate dihydrate) | 12 µg |
| Budesonide | 100 µg |
| Lactose | up to 5, 12.5 or 25 mg |

We claim:

1. A medicament containing as active ingredients effective amounts of a physiologically acceptable salt of formoterol or a solvate thereof, and budesonide wherein the molar ratio of the formoterol component to the budesonide component is in the range from 1:4 to 1:70.

2. A pharmaceutical composition which comprises effective amounts of a physiologically acceptable salt of formoterol or a solvate thereof, and budesonide wherein the molar ratio of the formoterol component to the budesonide component is in the range from 1:4 to 1:70, together with a pharmaceutically acceptable carrier.

3. A method for the treatment of asthma and other inflammatory respiratory disorders which comprises administering by inhalation to a host in need of such treatment effective amounts of a physiologically acceptable salt of formoterol or a solvate thereof, and budesonide wherein the molar ratio of the formoterol component to the budesonide component is in the range from 1:4 to 1.70.

4. The method according to claim 3, wherein the effective amount of the physiologically acceptable salt of formoterol or solvate thereof is 6–100 µg per day, and the effective amount of budesonide is 50–4800 µg per day.

5. The method according to claim 4 wherein the effective amount of the physiologically acceptable salt of formoterol or solvate thereof is 6–48 µg per day, and the effective amount of budesonide is 100–1600 µg per day.

6. The medicament of claim 1 wherein the active ingredients are in dry powder form.

7. The medicament of claim 1 or 6 wherein the formoterol is in the form of the fumarate dihydrate.

8. The pharmaceutical composition of claim 2 wherein the formoterol is in the form of the fumarate dihydrate.

9. The method according to any one of claims 3–5 wherein the administration is performed from a dry powder inhaler.

10. The method according to claim 9 wherein the inhaler is a Turbuhaler®.

11. The method according to any one of claims 3–5 wherein the administration is performed from a metered dose inhaler.

12. The method according to any one of claims 3–5 wherein the formoterol is in the form of the fumarate dihydrate.

13. A pharmaceutical composition according to claim 2 wherein the pharmaceutically acceptable carrier is lactose.

14. A pharmaceutical composition according to claim 13 in dosage unit form.

15. The method according to any one of claims 3–5 wherein the administration is performed with a nebulizer.

16. The method according to any one of claims 3–5 wherein the formoterol component and the budesonide component are administered simultaneously.

17. The method according to any one of claims 3–5 wherein the formoterol component is administered in admixture with the budesonide component.

18. The method according to any one of claims 3–5 wherein the formoterol component and the budesonide component are administered sequentially.

19. The method according to any one of claims 3–5 wherein the formoterol component and the budesonide component are administered separately.

* * * * *